(12) United States Patent
Springate

(10) Patent No.: US 8,466,125 B2
(45) Date of Patent: Jun. 18, 2013

(54) PHARMACEUTICAL COMPOSITIONS COMPRISING MODIFIED FUCANS AND METHODS RELATING THERETO

(75) Inventor: Christopher Michael Kevin Springate, Vancouver (CA)

(73) Assignee: ARC Medical Devices Inc., Vancouver, BC (CA)

( * ) Notice: Subject to any disclaimer, the term of this patent is extended or adjusted under 35 U.S.C. 154(b) by 126 days.

(21) Appl. No.: 12/843,992

(22) Filed: Jul. 27, 2010

(65) Prior Publication Data

US 2011/0021457 A1    Jan. 27, 2011

Related U.S. Application Data

(60) Provisional application No. 61/228,929, filed on Jul. 27, 2009.

(51) Int. Cl.
| | |
|---|---|
| *A61K 8/73* | (2006.01) |
| *A61K 9/14* | (2006.01) |
| *A61K 9/19* | (2006.01) |
| *A61K 9/06* | (2006.01) |
| *A61K 9/08* | (2006.01) |
| *A61K 31/715* | (2006.01) |
| *A61K 31/737* | (2006.01) |

(52) U.S. Cl.
USPC .......................................................... 514/54

(58) Field of Classification Search
USPC .......................................................... 514/54
See application file for complete search history.

(56) References Cited

U.S. PATENT DOCUMENTS 5,948,405 A * 9/1999 Cedro et al. ................. 424/115
6,559,131 B1 * 5/2003 Senni et al. .................... 514/54

FOREIGN PATENT DOCUMENTS

| | | |
|---|---|---|
| CA | 2 458 853 A1 | 3/2003 |
| CA | 2 527 429 A1 | 12/2004 |
| CA | 2 623 471 A1 | 3/2006 |
| CN | 1547478 A | 11/2004 |
| CN | 1829501 A | 9/2006 |
| EP | 1 226 826 A1 | 7/2002 |
| WO | 2007/028256 A2 | 3/2007 |

OTHER PUBLICATIONS

Pereira et al, Journal of Biological Chemistry, 1999, 7656-67.*
Li et al, Molecules 2008, 13, 1671-95.*
Durig et al, Thrombosis Research, 1997, 85(6), 479-91.*
Cetin et al., "Protective effect of fucoidin (a neutrophil rolling inhibitor) on ischemia reperfusion injury: experimental study in rat epigastric island flaps", Annals of Plastic Surgery (Nov. 2001), 47:540-546.
Cumashi et al. "A comparative study of the anti-inflammatory, anticoagulant, antiangiogenic, and antiadhesive activies of nine different fucoidans from brown seaweeds", Glycobiology (Feb. 12, 2007), 17:541-552.
ARC Pharmaceuticals, "Fucoidan Concentrate Medical Device", ARC Pharmaceuticals Inc. (Nov. 2008), retrieved from www.slideshare.net/ARC_Pharma/documents).
Kuznetsova, T.A., "Fucoidan extracted from Fucus Evanescens brown algea corrects immunity and hermostasis diorders in experimental endotoxemia", Bulletin of Experimental Biology and Medicine (Jan. 2009), 147(1):71-74.
PCT International Search Report, date of mailing Nov. 2, 2010, pp. 1-7.
PCT Written Opinion, date of mailing Nov. 2, 2010, pp. 1-5.
European Search Report, Application No. 10803778.9, Date of Mailing: Jan. 30, 2013, pp. 7.
"Scientific Presentation Abstracts European College of Veterinary Surgeons, 18th Annual Scientific Meeting to be Held Jul. 2-4, 2009, Nantes, France," Veterinary Surgery, vol. 38, No. 4, Jun. 1, 2009, pp. E1-E22.

* cited by examiner

*Primary Examiner* — Shaojia Anna Jiang
*Assistant Examiner* — Ganapathy Krishnan
(74) *Attorney, Agent, or Firm* — Graybeal Jackson LLP

(57) ABSTRACT

Compositions and methods relating to fucan agents useful for the treatment, prevention, inhibition, etc., of fibrous adhesions or other diseases.

31 Claims, No Drawings

PHARMACEUTICAL COMPOSITIONS COMPRISING MODIFIED FUCANS AND METHODS RELATING THERETO

CROSS-REFERENCE TO RELATED APPLICATIONS

The present application claims priority from U.S. provisional patent application No. 61/228,929, filed Jul. 27, 2009. These and all other references set forth herein are incorporated herein by reference.

TABLE OF CONTENTS

The following is a Table of Contents to assist review of the present application:
CROSS-REFERENCE TO OTHER APPLICATIONS
TABLE OF CONTENTS
BACKGROUND
SUMMARY
DETAILED DESCRIPTION
General Discussion Of Exemplary Agents
Fucans
Films
Gels
Instillates
Discussion Of Quantitative Effectiveness Of Anti-Fibrous Adhesion Agents
Further Exemplary Embodiments
EXAMPLES
CLAIMS
ABSTRACT

BACKGROUND

A fibrous adhesion is a type of scar that forms between two parts of the body, usually after surgery (surgical adhesion). Fibrous adhesions can cause severe problems. For example, fibrous adhesions involving the female reproductive organs (ovaries, Fallopian tubes) can cause infertility, dyspareunia and severe pelvic pain. Fibrous adhesions that occur in the bowel can cause bowel obstruction or blockage, and fibrous adhesions can also form in other places such as around the heart, spine and in the hand. In addition to surgery, fibrous adhesions can be caused for example by endometriosis, infection, chemotherapy, radiation, trauma and cancer.

A variety of fibrous adhesions are discussed in this document. Terms such as surgical adhesions, post-surgical adhesions, postoperative adhesions, adhesions due to pelvic inflammatory disease, adhesions due to mechanical injury, adhesions due to radiation, adhesions due to radiation treatment, adhesions due to trauma, and adhesions due to presence of foreign material all refer to adherence of tissues to each other due to a similar mechanism and are all included in the term fibrous adhesions.

Fibrous adhesion formation is a complex process in which tissues that are normally separated in the body grow into each other. Surgical adhesions (also known as post-surgical adhesions) develop from the otherwise normal wound healing response of the tissues to trauma and have been reported to occur in over two-thirds of all abdominal surgical patients (Ellis, H., *Surg. Gynecol. Obstet.* 133: 497 (1971)). The consequences of these fibrous adhesions are varied and depend upon the surgical site or other site, such as a disease site, involved. Problems may include chronic pain, obstruction of the intestines and even an increased risk of death after cardiac surgery (diZerega, G. S., *Prog. Clin. Biol. Res.* 381: 1-18 (1993); diZerega, G. S., *Fertil. Steril.* 61:219-235 (1994); Dobell, A. R., Jain, A. K., *Ann. Thorac. Surg.* 37: 273-278 (1984)). In women of reproductive age, fibrous adhesions involving the uterus, fallopian tubes or ovaries are estimated to account for approximately 20% of all infertility cases (Holtz, G., *Fertil. Steril.* 41: 497-507 (1984); Weibel, M. A. and Majno, G. *Am. J. Surg.* 126: 345-353 (1973)).

The process of fibrous adhesion formation initially involves the establishment of a fibrin framework and normal tissue repair. The normal repair process allows for fibrinolysis alongside mesothelial repair. However, in fibrous adhesion formation the fibrin matrix matures as fibroblasts proliferate into the network and angiogenesis occurs resulting in the establishment of an organized fibrous adhesion within about 3 to 5 days (Buckman, R. F., et al., *J. Surg. Res.* 21: 67-76 (1976); Raferty, A. T., *J. Anat.* 129: 659-664 (1979)). Inflammatory processes include neutrophil activation in the traumatised tissues, fibrin deposition and bonding of adjacent tissues, macrophage invasion, fibroblast proliferation into the area, collagen deposition, angiogenesis and the establishment of permanent fibrous adhesion tissues.

Various attempts have been made to prevent surgical adhesions. These involve pharmacological approaches targeted at influencing the biochemical and cellular events that accompany surgical traumas well as barrier methods for the separation of affected tissues. For example, the use of peritoneal lavage, heparinized solutions, procoagulants, modification of surgical techniques such as the use of microscopic or laparoscopic surgical techniques, the elimination of talc from surgical gloves, the use of smaller sutures and the use of physical barriers (films, gels or solutions) aiming to minimize apposition of serosal surfaces, have all been attempted. Currently, preventive therapies also include prevention of fibrin deposition, reduction of inflammation (steroidal and non-steroidal anti-inflammatory drugs) and removal of fibrin deposits.

Interventional attempts to prevent the formation of post-surgical adhesions have included the use of hydroflotation techniques or barrier devices. Hydroflotation involves the instillation of large volumes of polymer solutions such as dextran (Adhesion Study Group, *Fertil. Steril.* 40:612-619 (1983)), or carboxymethyl cellulose (Elkins, T. E., et al., *Fertil. Steril.* 41:926-928 (1984)), into the surgical space in an attempt to keep the organs apart. Synthetic barrier membranes made from oxidized regenerated cellulose (e.g., Interceed™), polytetrafluoroethylene (Gore-tex surgical membrane) and fully resorbable membranes made from a modified hyaluronic acid/carboxymethylcellulose (HA/CMC) combination (Seprafilm™) have also been used to reduce post-surgical adhesion formation in both animals and humans (Burns, J. W., et al., *Eur. J. Surg. Suppl.* 577: 40-48 (1997); Burns, J. W., et al., *Fertil. Steril.* 66:814-821 (1996); Becker, J. M., et al., *J. Am. Coll. Surg.* 183:297-306 (1996)). The success of these HA/CMC membranes may derive from their ability to provide tissue separation during the peritoneal wound repair process when fibrous adhesions form. The membranes were observed to form a clear viscous coating on the injured tissue for 3-5 days after application, a time period that is compatible with the time course of post-surgical adhesion formation (Ellis, H., *Br. J. Surg.* 50: 10-16 (1963)). Unfortunately, limited success has been seen with these methods.

Peritonitis involves inflammation of the peritoneum. Peritonitis can cause severe problems. For example, abdominal pain, abdominal tenderness and abdominal guarding. Peritonitis may involve spontaneous, anatomic and/or peritoneal dialysis related inflammation. Peritonitis may involve an infection, for example, perforation of a hollow viscus, disruption of the peritoneum, spontaneous bacterial peritonitis, and systemic infections may result in infection and peritonitis. Peritonitis may also not involve an infection, for example, leakage of sterile body fluids into the peritoneum, and sterile abdominal surgery may result in peritonitis. Various attempts have been made to prevent and/or treat peritonitis. For example, general supportive measures such as intravenous rehydration, antibiotics, and surgery. There is an unmet need for compounds, compositions, methods and the like (including delivery approaches) to inhibit, or otherwise treat and/or prevent, peritonitis, preferably more effectively with few side effects.

Ischemia or ischaemia involves a restriction in blood supply, which may include a shortage of supply of oxygen, glucose and other components required for proper tissue function, resulting in damage and/or dysfunction of tissue. Ischemia can cause severe problems. For example, tissues can become anoxic, necrotic, and clots can form. Various attempts have been made to prevent and/or treat ischemia. For example, restoration of blood flow, or reperfusion. Restoration of blood, however, involves the reintroduction of oxygen, which can cause additional damage due to the production of free radicals, resulting in reperfusion injury. Reperfusion injury can cause severe problems. There is an unmet need for compounds, compositions, methods and the like (including delivery approaches) to inhibit, or otherwise treat and/or prevent, ischemia, and/or reperfusion injury, preferably more effectively with few side effects.

Endotoxemia is the presence of endotoxins in the blood. Endotoxemia can cause severe problems. For example, endotoxemia can lead to septic shock. There is an unmet need for compounds, compositions, methods and the like (including delivery approaches) to inhibit, or otherwise treat and/or prevent, endotoxemia, preferably more effectively with few side effects.

Keloid trait causes wounds to heal with raised scars. Keloid traits' raised scars involve abnormal fibrous scarring. Keloid trait causes severe problems. For example, pain and disfigurement. There is an unmet need for compounds, compositions, methods and the like (including delivery approaches) to inhibit, or otherwise treat and/or prevent, keloid trait and its resulting raised scars, preferably more effectively with few side effects.

Keloid (keloid scar) is a type of scar that expands in growths over normal skin. Keloids involve abnormal collagen growth, including type I and type III collage abnormal growth. Keloids cause severe problems. For example, keloids cause pain, itchiness, and if infected may ulcerate. Attempts have been made to treat or prevent keloids including the use of surgery, dressings, steroid injections and laser therapy. There is an unmet need for compounds, compositions, methods and the like (including delivery approaches) to inhibit, or otherwise treat and/or prevent, keloids, preferably more effectively with few side effects.

Dermatitis includes inflammation of the skin including atopic dermatitis and contact dermatitis. For example, contact dermatitis involves localized rash and/or irritation of the skin following contact of the skin with a foreign substance. For example, atopic dermatitis is a chronically relapsing, pruritic skin disease. Atopic dermatitis is sometimes called prurigo Besnier, neurodermitis, endogenous eczema, flexural eczema, infantile eczema, childhood eczema and prurigo diathsique. Eczema is a disease in a form of dermatitis. Other types of dermatitis include spongiotic dermatitis, seborrhoeic dermatitis (dandruff), dyswhidrotic dermatitis (pompholyx), urticaria, vesicular dermatitis (bullous dermatitis), and popular urticaria. Dermatitis can cause severe problems. For example, dry skin, skin rashes, skin edema, skin redness, skin itchiness, skin crusting, cracking, blistering, oozing and bleeding. Attempts have been made to treat or prevent dermatitis including the use of corticosteroids and coal tars. There is an unmet need for compounds, compositions, methods and the like (including delivery approaches) to inhibit, or otherwise treat and/or prevent, dermatitis including atopic dermatitis, eczema, contact dermatitis, spongiotic dermatitis, seborrhoeic dermatitis, dyswhidrotic dermatitis, urticaria, vesicular dermatitis, and popular urticaria, preferably more effectively with few side effects.

Rosacea is a chronic disease or condition typically characterized by facial erythema. Rosacae can cause severe problems. For example, rosacae typically begins as redness on the forehead, nose or cheeks and can also cause redness on the neck, ears, scalp and chest. For example, rosacae can cause additional symptoms including telangiectasia, papules, pustules, painful sensations, and in advanced cases rhinophyma (red lobulated nose) may develop. Rosacea subtypes include erythematotelangiectatic rosacea, papulopustular rosacea, phymatous rosacea, and ocular rosacea. Attempts have been made to treat or prevent rosacea including the use of anti-inflammatories and antibiotics. There is an unmet need for compounds, compositions, methods and the like (including delivery approaches) to inhibit, or otherwise treat and/or prevent, rosacea including its erythematotelangiectatic, papulopustular, rosacea and ocular subtypes, preferably more effectively with few side effects.

There is an unmet need for compounds, compositions, methods and the like (including delivery approaches) to inhibit, or otherwise treat and/or prevent, the formation of fibrous adhesions and/or the other diseases and/or conditions discussed herein and related diseases and/or conditions, preferably more effectively with few side effects. The present compounds, compositions, methods, etc., provide one or more of these advantages.

SUMMARY

The present compositions, methods, etc., herein comprise compositions and methods, etc., comprising one or more agents against fibrous adhesions or other diseases discussed herein, for the treatment of surgical adhesions or such other diseases or conditions. The anti-disease agents provide significant therapeutic effect against fibrous adhesions or other conditions while typically also providing low side effects. Further, since a variety of different agents are discussed, various combinations of the agents can be selected as desired to reduce side effects in a patient potentially suffering from other diseases or conditions, and/or to provide other beneficial healthful or therapeutic effects, such as compositions that both inhibit fibrous adhesions and also treat cancer or arthritis or swelling or any of the variety of other diseases or conditions that can also be treated by one or more of the anti-fibrous adhesion agents herein. The compositions herein are also useful for the treatment of fibrous growths and conditions such as keloid trait that share similar biology with fibrous adhesions, and other diseases and conditions as discussed herein. Accordingly, the discussion herein applies to such fibrous growths as well.

In certain embodiments the present compositions, methods, etc., herein include treatment, prevention, inhibition, etc., using selected modified fucans (or fucan compositions) comprising specified combinations of components including usually a total carbohydrate content of more than about 40% w/w; a fucose content as a percentage of total carbohydrate content between about 40 to 100%; a galactose content as a percentage of total carbohydrate content between about 0 to 60%; a sugar content excluding (i.e., other than) fucose and galactose as a percentage of total carbohydrate content between about 0 to 20%; an acetyl group to fucose monomer ratio of less than about 40%; a molecular weight distribution such that the portion of modified fucans from about 0 to 5,000 g/mol comprises less than about 30% w/w; a molecular weight distribution such that the portion of modified fucans from about 5,000 to 60,000 g/mol comprises less than about 50%; a molecular weight distribution such that the portion of modified fucans from about 60,000 to 200,000 g/mol comprises less than about 40% w/w; a molecular weight distribution such that the portion of modified fucans from about 200,000 to 1,600,000 g/mol comprises less than about 50% w/w; a molecular weight distribution such that the portion of modified fucans from more than about 1,600,000 g/mol comprises less than 50% w/w; a sulphate content between about 10 to 50% w/w; and/or a water content of less than about 20% w/w. The selected modified fucans also include modified fucans that when made up to a 0.1% w/v solution result in a solution with a pH of about 4 to 8. The composition will typically include at least one pharmaceutically acceptable excipient, filler, carrier or diluent. The pharmaceutically acceptable excipient, filler, carrier or diluent can if desired be selected from the group consisting of a pluronic, cellulose, alginate, acrylate, hyaluronic acid, polyethylene glycol, and chitosan.

Accordingly, the compositions, methods, etc., herein comprises modified fucans for treating inflammatory disease including arthritis, and for treating fibrous adhesions, including surgical adhesions, as well as for treating peritonitis, ischemia, reperfusion injury, endotoxemia, keloid trait scarring, keloids, dermatitis, and rosacea.

Thus, the present compositions, methods, etc., herein provide pharmaceutical compositions configured to inhibit fibrous adhesions, the compositions comprising a therapeutically effective amount of a modified fucan as discussed herein selected to inhibit the fibrous adhesion, optionally a therapeutically effective amount of at least one of the therapeutically effective agents herein selected to inhibit the fibrous adhesion, and at least one pharmaceutically acceptable excipient, filler, carrier or diluent. The pharmaceutically acceptable excipient, filler, carrier or diluent can if desired be selected from the group consisting of a pluronic, cellulose, alginate, acrylate, hyaluronic acid, polyethylene glycol, and chitosan.

The present compositions and methods, etc., comprise selected modified fucans for the treatment of peritonitis, ischemia, reperfusion injury, endotoxemia, keloid trait scarring, keloids, dermatitis, and rosacea. Modified fucans provide significant therapeutic effect against peritonitis, ischemia, reperfusion injury, endotoxemia, keloid trait scarring, keloids, dermatitis, and rosacea while typically also providing low side effects. In one aspect, the compositions, etc., provide methods of treating or preventing peritonitis, ischemia, reperfusion injury, endotoxemia, keloid trait scarring, keloids, dermatitis, and rosacea in a subject or patient comprising administering a therapeutically effective amount of the selected modified fucan to the subject or patient.

In some embodiments, the subject or patient is an animal, such as a human, dog, cat, horse, cow, camel or other mammal, or bird, reptile or other animal. The site can be the animal as a whole, or a localized site such as within an abdomen, limb, spine, head, reproductive tract, gastrointestinal tract, pulmonary system, thoracic cavity, cardiac or vascular system, urinary system, or an intraabdominal site for the treatment of peritonitis, ischemia and reperfusion injury, or such as the vasculature for the treatment of endotoxemia, or such as a topical site of disease for the treatment of keloid trait scarring, keloids, dermatitis, and rosacea, or any other desired site. The site can be the animal as a whole, or a specific site within an abdomen, limb, within a spine, a head, a reproductive tract, a gastrointestinal tract, a pulmonary system, thoracic cavity, cardiac or vascular system, a urinary system, on the skin, or any other system or location as desired. The treatment site can be a surgical site, a pelvic inflammatory disease site, a mechanical injury site, a radiation exposure site, a site suffering presence of a foreign material or any other desired site.

The selected modified fucan can be substantially continuously administered to the disease site via controlled release from a polymeric dosage form. The administration form can comprise a film, instillate, patch, paste, microsphere, implant, gel, spray or liquid, solution, suspension, which can be in Lactated Ringers Injection USP. The selected modified fucan can be administered in combination with a second agent, which can be any one or more of the other agents herein or any other therapeutic agent.

The compositions and methods, etc., can be used in the manufacture of a medicament including a medical composition or device for reducing symptoms associated with fibrous adhesions, peritonitis, ischemia, reperfusion injury, endotoxemia, keloid trait scarring, keloids, dermatitis, and rosacea in a subject or patient. Medicaments can be made by combining a pharmaceutically effective amount of modified fucan and a pharmaceutically acceptable excipients, diluent or buffer, and can comprise an additional anti-disease agent(s).

The modified fucan compositions herein can be used in combination with a second therapeutic agent such as a therapeutically effective amount one or more of an alginic acid, a doxycycline, a cortisone, an estramustine, a melezitose, a succinic acid, a meclofenamate, a palmitic acid, a dextran sulfate, collagen, a budesonide, an enalapril such as enalapril maleate, a nabumetone, a statin such as simvastatin, a captopril, a chitosan, aminocycline, a methotrexate, a cisplatin, an ibuprofen, an erythromycin, a tetracycline, an SDF-1 inhibitor such as an anti-SDF-1 antisense oligonucleotides (ASO), an anti-SDF-1 small molecule RNA, an anti-SDF-1 siRNA, an anti-SDF-1 ribozyme, an anti-SDF-1 aptamer, a small molecule inhibitor of SDF-1, an anti-SDF-1 antibody such as anti-hSDF-1/PBSF, a rapamycin, a hydroxypropylcellulose, a busulfan, a cyclophosphamide, a dacarbazine, a hydroxyurea, a mitotane, a docetaxel, a vinblastine sulfate, a MG132, a nimesulide, a diclofenac, a tenoxicam, an indomethacin, an acetylsalicylic acid, a diflusinal, a betamethasone, a dexamethasone, a deferoxamine mesylate, a retinoic acid, a heparin, a pentoxifylline, a streptokinase, a TGF-beta, a TIMP-2, a dextrose, a Dextran T70, a starch, a quercetin dihydrate, a caffeine, a leflunomide, a carrageenan such as iota-carrageenan or lambda-carrageenan, a hydroxypropylcellulose, a stachyose, a chondroitin sulfate A.

The agents can also be an anti-neoplastic agent, an anti-inflammatory agent, an iron-chelating agent, a triene macrolide antibiotic, a 3-hydroxy-3-methylgluteryl-CoA reductase inhibitor, a retinoid, an antithrombotic, an anticoagulant, a plasminogen activator, a cytokine, a matrix metalloproteinase inhibitor, a tetracycline, an ACE inhibitor, a dextran sugar, or a carrageenan, alkylating agent, an antimetabolite, a ribonucleotide reductase inhibitor, a cytotoxic antibiotic, a taxane, a vincalkaloid, or a protease inhibitor, a COX-2 inhibitor, a fenamate, an oxicam, an acetyl acid derivative, a salicylic acid derivative, or a corticosteroid.

As noted elsewhere, the various aspects and embodiments herein can be features, etc., can be mixed and matched, combined and permuted in any desired manner. Thus, the particular agents, disease targets, above and below, etc., can be combined, etc., as appropriate even if they do not appear together in the same paragraph. Some discussion of certain suitable secondary agents can be found, for example, in U.S. Pat. No. 6,812,220, issued Nov. 2, 2004; U.S. Pat. No. 7,163,930, issued Jan. 16, 2007; US published application no. 20080063682; and, PCT publication no. WO2004105737, PCT publication no. WO2006032143, all of which are incorporated herein by reference.

In still yet another further aspect, the present compositions, methods, etc., herein provides kits. The kits can comprise a vessel containing the compositions herein and a label comprising instructions for pharmaceutical use of the compositions to inhibit fibrous adhesions. The label can be a government approved label such as an FDA approved label, for example the FDA standards in place on Jul. 1, 2009. The vessel can be a vial configured to hold an instillate or any other desired composition form herein. The label further can comprise instructions for pharmaceutical use of the compositions to treat at least one of a non-fibrous adhesion disease or non-fibrous adhesion condition.

These and other aspects, features and embodiments are set forth within this application, including the following Detailed Description and attached drawings.

DETAILED DESCRIPTION

General Discussion of Exemplary Agents

In certain embodiments the present compositions, methods, etc., herein include treatment, prevention, inhibition, etc., of diseases or conditions such as fibrous adhesions, including surgical adhesions, using selected modified fucans comprising specified combinations of components including usually a total carbohydrate content of more than about 40% w/w; a fucose content as a percentage of total carbohydrate content between about 40 to 100%; a galactose content as a percentage of total carbohydrate content between about 0 to 60%; a sugar content excluding fucose and galactose as a percentage of total carbohydrate content between about 0 to 20%; an acetyl group to fucose monomer ratio of less than about 40%; a molecular weight distribution such that the portion of modified fucans from about 0 to 5,000 g/mol comprises less than about 30% w/w; a molecular weight distribution such that the portion of modified fucans from about 5,000 to 60,000 g/mol comprises less than about 50%; a molecular weight distribution such that the portion of modified fucans from about 60,000 to 200,000 g/mol comprises less than about 40% w/w; a molecular weight distribution such that the portion of modified fucans from about 200,000 to 1,600,000 g/mol comprises less than about 50% w/w; a molecular weight distribution such that the portion of modified fucans from more than about 1,600,000 g/mol comprises less than 50% w/w; a sulphate content between about 10 to 50% w/w; and/or a water content of less than about 20% w/w. The selected modified fucans also include modified fucans that when made up to a 0.1% w/v solution result in a solution with a pH of about 4 to 8. The compositions, methods, etc., herein can further comprises the modified fucans for treating inflammatory disease including arthritis, and peritonitis, ischemia, endotoxemia, keloid trait/raised scars, keloids (keloid scars), dermatitis (including spongiotic dermatitis, seborrhoeic dermatitis (dandruff), dyswhidrotic dermatitis (pompholyx), urticaria, vesicular dermatitis (bullous dermatitis), and popular urticaria), rosacea (e.g., erythematotelangiectatic rosacea, papulopustular rosacea, phymatous rosacea, and ocular rosacea).

The compositions are medical compositions, which can be either pharmaceutical or nutraceutical compositions. As used herein, pharmaceutical compositions means pharmacological agents (drugs) and medical devices comprised of or containing the compositions herein. Pharmaceutical compositions are different from nutraceutical compositions which are considered to be items such as medical foods.

The compositions can also comprise secondary agents, e.g., to treat, inhibit or prevent, the formation of fibrous adhesions or other disease discussed herein. Such adhesions may form following surgery, following trauma, or following radiation or chemotherapy, or as a result of any other cause, by application of the agent(s) to the tissue of an animal, including a human, dog, cat, horse, cow, or other mammal, or bird, reptile or other animal at site suspected of developing a fibrous adhesion, for example sites actually having a fibrous adhesion, sites unduly subject to developing a fibrous adhesion, for example due to exposure to radiation, surgery, disease, or injury, and sites in the process of developing or expanding fibrous adhesions. Each secondary agent listed includes the agent and all its derivatives, salts, and analogues without exclusion unless expressly stated otherwise. The secondary agents can be administered in different formulations for the inhibition of fibrous adhesions. These compositions can if desired allow for release of effective doses of the secondary agents at the disease sites only, in order to reduce toxicity that may be associated with systemic delivery of some of these compounds. These compositions can also comprise polymeric formulations of an secondary agent herein (including all derivatives, salts and analogues thereof), or other formulations as desired, which can provide sustained release of the secondary agent at the potential fibrous adhesion site. The compositions can be administered to a site directly, systemically or otherwise as desired. In certain embodiments, the compositions herein do not include any antisense oligonucleotides or other oligonucleotide agents such as gene therapy nucleotides.

The embodiments herein can include identifying a fibrous or non-fibrous adhesion disease or condition, then selecting and administering a composition comprising the compositions herein. In some embodiments, the compositions and methods can further comprise selecting two or more of the agents herein, such that one has primary effect against the disease or condition and the other has primary effect. Exemplary non-fibrous adhesion diseases or conditions include cancers, PID, radiation exposures, mechanical and other injuries, arthritis, surgery, topical conditions, diseases and conditions of the GI tract, for example those that have substantial risk of blockages or other mechanically disruptive symptoms, etc.

Within certain embodiments, the anti-fibrous adhesion agents may be formulated along with other compounds or compositions, such as, for example, an ointment, solution, cream, powder lotion, gel, spray, mousse, coating, wrap, paste, barrier, implant, microsphere, microparticle, film, particulate, liquid, implant films, instillate formulations and the like. Routes and sites of administration include orally, systemically, intraocularly, subcutaneously, intraperitoneally, intramuscularly, intraarticularly, intralesionally, intravaginally, rectally or topically, such as in a patch.

The compositions herein can be provided in suitable vessels or containers, which in turn can be provided in kits and can also be provided with a label, preferably a label approved by an appropriate government regulatory agency such as the Food and Drug Administration in the United States of America. The label can comprise instructions for pharmaceutical use of the composition. The vessel can be, for example, a vial, and can be configured to provide the composition(s) as films, gels, instillates, or other forms discussed herein or as otherwise desired.

The compound or composition given with the anti-fibrous adhesion agents may function as a carrier and/or as a physical barrier, which may be either polymeric or non-polymeric. The compositions discussed herein also comprise agents (or any combination of agents from the list of agents discussed herein including fucoidan, modified fucan or other modified fucan) alone or in aqueous solution, or non-aqueous solution, or dispersed as a suspension within a vehicle or carrier. Representative examples of polymeric carriers, barriers and excipients include chitosan, polytetrafluoroethylene, poly(lactic acid), poly-(ethylene vinyl acetate), poly(glycolic acid), copolymers of ethylene and vinyl acetate, polyethylene glycol, methoxypolyethylene glycol, polycaprolactone, copolymers of lactic acid and glycolic acid, copolymers of poly(lactic acid) and poly(caprolactone), gelatin, collagen, celluloses, albumen, pluronics, poly-(valerolactone), poly-(anhydrides), polysaccharides, alginic acids such as alginates, hyaluronic acid, injectable excipients other polymeric based vehicles and copolymers, derivatives mixtures and blends thereof. Representative examples of other suitable carriers include ethanol, glycols including ethylene glycol, propylene glycol or Transcutol®, mixtures of ethanol and glycols, isopropyl myristate or isopropyl palmitate, mixtures of ethanol and isopropyl myristate or isopropyl palmitate. Such polymers may, themselves, provide anti-adhesion activity in certain compositions.

Exemplary secondary agents include NSAIDs, COX-2 inhibitors, nimesulide, fenamates including meclofenamic acid, meclofenamate, diclofenac, oxicams including tenoxicam, acetyl acid derivatives including indomethacins, salicylic acid derivatives including acetylsalicylic acid and diflunisal, pyrazalones including phenylbutazone, corticosteroids including dexamethasone, alkylating agents including Busulfan, cyclophosphamide, estramustine, cisplatin and dacarbazine, antimetabolites including methotrexate, ribonucleotide reductase inhibitors including hydroxyurea, cytotoxic antibiotics including mitotane, taxanes, topoisomerase inhibitors including docetaxel, vincalkaloids and analogues including vinblastine, proteasome inhibitors including MG132, iron-chelating agents including deferoxamine mesylate, 3-Hydroxy-3-Methylgluteryl-CoA Reductase Inhibitors including statins and simvastatin, retinoids and retinoid analogues including all-trans-retinoic acid, antithrombotics including heparin sodium, low molecular weight heparins, anticoagulants including pentoxifylline, plasminogen activators including streptokinase, cytokines including transforming growth factor-beta (TGF-β), matrix metalloproteinase inhibitors, tissue inhibitors of matrix metalloproteinases (TIMPs) including TIMP-2, tetracyclines including tetracycline minocycline and doxycycline, angiotensin-converting enzyme (ACE) inhibitors including captopril and enalaprils including salts thereof such as enalapril maleate. Certain other desired agents include: leflunomide (Arava), erythromycin, dextran sulfate alginic acid, dextrose, Dextran T70, starch, quercetin dihydrate, caffeine, t-carrageenan, λ-carrageenan, hydroxypropylcellulose, stachyose, and chondroitin sulfate A. Discussion of these secondary agents can be found, for example, in PCT publication no. WO2006032143.

Fucans

Fucans (including fucoidan and modified fucans) are high molecular weight sulphated polysaccharides extracted from brown seaweeds, Percival, E., and McDowell, R. H., Chemistry and Enzymology of Marine Algal Polysaccharides, pp. 157-175 (Academic Press, New York, 1967), and as is well known can be found from other sources such as in the taxonomic families of Fucales and Laminariaceae, or from other marine algae and seaweeds and echinoderms, sea cucumbers, sea urchins or other sources as desired including synthetic sources. Fucoidan (or fucoidin) indicates modified fucans derived from brown seaweed or other sources. See USPA 2003064958. Fucans can be alone, or in a mixture, for example in a mixture of sugars such as xylose, galactose, glucose and/or mannose. These sugars are known to be contained in the marine algae and may be extracted with the modified fucan. Duarte, Maria E R., Cardoso, Marc A., Noseda, Miguel D., Cerezo, Alberto S., "Structural studies on fucoidans from the brown seaweed *Sargassum stenophyllum*". Carbohydrate Research: 2001 (333): 281-29. Other sulphated modified fucans including linear, branched and linear sulphated modified fucans are reported to have differential anticoagulant activity (Pereira, M. S., *J. Biol. Chem.* 12: 7656-67 (1999)).

Fucans such as fucoidan can be obtained from a variety of species of brown algae including but not limited to: *Adenocystis utricularis, Ascophyllum nodosum, Chorda filum, Cladosiphon okamuranus, Cystoseirabies marina, Ecklonia kurome, Fucus evanescens, Fucus vesiculosis, Hizikia fusiforme, Kjellmaniella crassifolia, Laminaria brasiliensis, Laminaria cichorioides, Laminaria japonica* (commonly called Kombu) *Laminaria saccharina, Pelvetia fastigiata, Sargassum stenophylum, Sargassum thunbergii*, and *Undaria pinnatifida*. These species are all from the taxonomic class Phaeophyceae and the majority of these species fall into the families of Fucales and Laminariaceae.

Films

The agents discussed herein can be formulated as a film suitable for direct application to tissue of an animal, including a human, for the treatment of fibrous adhesions. The desired properties of the film include that it is thin, flexible, has the ability to be handled and is able to be affixed to tissue. Each agent discussed herein can also be incorporated into a polymer to create a film. The properties of the polymeric film formulation can be enhanced with the addition of suitable excipients. In one embodiment, the agent can be combined with hyaluronic acid polymer to make a film. Excipients which can be added include 1-ethyl-3-[3-(dimethylamino)propyl]carbodiimide (EDAC) and glycerol.

An embodiment herein is the incorporation of the agent to produce a drug (agent) loaded film comprising 0.001%-99% w/w drug, 50%-99% w/w drug, 0.001%-50% w/w drug, 10%-50% w/w drug, 30%-40% w/w drug, 0.001%-10% w/w drug, 1%-10% w/w drug, 0.001%-1% w/w drug, 1%-5% w/w drug, 1%-2% w/w drug, or other concentrations discussed herein. One embodiment comprises the incorporation of the agent with hyaluronic acid yielding a 5% w/w drug loaded film, with the remainder of the film being made up of Hyaluronic acid, glycerol, and EDAC in approximately a 45:19:3 ratio.

Gels

Each agent discussed herein can be incorporated into a viscous solution, which herein will be referred to as a gel. This gel can be administered to a body cavity of an animal, including a human, and is efficacious for the inhibition or prevention of fibrous adhesion formation.

Desired properties of the gel include that it is viscous enough to be applied to a specific location and remain affixed there, thus it will not flow under its own weight; and that it can be administered to the preferred location with the use of a syringe or injected through a needle. In one embodiment gel comprises 5.5% w/v hyaluronic acid solution with the drug incorporated to yield a 0.001%-1% w/v gel, 1%-10% w/v gel, or 10%-50% w/v gel, or other concentrations as desired.

Instillates

Each composition discussed herein can also be dissolved or suspended in a liquid, which can be administered into a body cavity of an animal, including a human, and used to inhibit, treat, prevent, etc., the formation, including the increased growth, of fibrous adhesions. These formulations are herein referred to as instillate formulations. These formulations can, for example, be administered intra-abdominally following a surgical procedure into a patient to prevent the formation of post-operative adhesions, or into/onto any other desired wound, disease, etc., site. This liquid can be a solvent and can subsequently produce a solution of the agent. Additionally, the solvent used to dissolve the agent may be water-based, and can be an electrolytic solution.

In some embodiments the instillate solution is a substantially non-viscous liquid, for example having a viscosity substantially similar to water or substantially similar to a physiological salt solution, capable of reaching substantially all areas of a specific body cavity where it is introduced. The desired mixture may incorporate at least one agent discussed herein into a liquid to produce a solution (or suspension, sol, etc.) at concentrations of between about 0.0001% w/v and 1% w/v, between 1% w/v and 2% w/v, 2% w/v and 5% w/v, 5% and 10% w/v, 10% w/v and 25% w/v, and 25% w/v and 50% w/v, or other concentrations as desired. In some embodiments the instillate solution may first be prepared as a concentrated solution (or suspension, sol, etc.) and then further diluted (for example with commercially available saline solution or Lactated Ringer's Injection USP or other solution) to form a substantially non-viscous liquid. The concentrated solution (or suspension, sol, etc.) may be prepared at concentrations of between about 1% w/v and 25%, between 1% w/v and 20% w/v, between 1% w/v and 15% w/v, between 1% w/v and 10% w/v, between 5% w/v and 10% w/v, and at 5% w/v, or other concentrations as desired.

Discussion of Quantitative Effectiveness of Anti-Fibrous Adhesion Agents:

In one embodiment, the efficacy of the given drug or drug combination can be assessed as a reduction of the average Total Adhesion Value (strength×area; "TAV") of the drug or combination versus a given standard, for example a drug-loaded sodium hyaluronate film versus a sham or a sodium hyaluronate film alone in the rat cecal-sidewall model for surgical fibrous adhesions. Other standards can include other films, solutions, etc., and other models, such as rabbit uterine horn model or effectiveness in humans. In various embodiments, the drugs can have an average TAV less than or equal to 0.01%, 1%, 5%, 10%, 25%, 50%, or 75% of the control's value, for example the hyaluronate film alone, using the rat cecal-sidewall model for surgical fibrous adhesions. In other measurement parameters, the drugs can inhibit substantially all fibrous adhesion formation in a patient.

Further Exemplary Embodiments

In some embodiments the pharmaceutical composition can be a solution, gel, sol or suspension and can have a total w/v fucan concentration of the composition of 0 to 10% w/v, 5% w/v, 0.001 and 1% w/v, 0.05% w/v, 0.03% w/v.

In certain embodiments the present compositions, methods, etc., herein include treatment, inhibition, etc. using modified fucans such as modified fucans including fucoidans that have been customized (modified fucans) to provide increased efficacy and/or decreased toxicity and/or improved handling characteristics including during processing, manufacturing, shipping and/or administration to patients including humans, animals, reptiles and birds. Modified fucans include modified fucans that have an appearance of white to off-white, white to light yellow, white to light orange, white to light green, and white to light brown. Modified fucans also include modified fucans that have a total carbohydrate content between about 30 to 100% w/w, 40 to 90% w/w, 50 to 80% w/w, 37 to 75% w/w and about 55 to 75% w/w. Modified fucans also include modified fucans that have a fucose content as a percentage of total carbohydrate content between about 20 to 100%, about 30 to 100%, 31 to 71% w/w, about 40 to 100%, about 50 to 100%, about 60 to 100%, about 70 to 100%, about 80 to 100%, about 90 to 100%, about 40 to 80%, about 50 to 70% and about 51 to 71%.

Modified fucans also include modified fucans that have a galactose content as a percentage of total carbohydrate content between about 0 to 70%, 9 to 46% w/w, about 10 to 60%, about 20 to 50%, about 25 to 45%, and about 26 to 46%. Modified fucans also include modified fucans that have a sugar content excluding fucose and galactose as a percentage of total carbohydrate content between about 0 to 59% w/w, 0 to 40%, 0 to 30%, 0 to 20%, 0 to 15%, about 0 to 10%, about 0 to 6%, and about 0 to 5%. Modified fucans also include modified fucans that have a sugar content excluding fucose as a percentage of total carbohydrate content between about 0 to 40%, 0 to 30%, about 0 to 20%, about 0 to 15%, about 0 to 10%, about 0 to 6%, and about 0 to 5%.

Modified fucans also include modified fucans that have acetyl group content of about 0 to 100% w/w, about 0 to 70% w/w, about 0 to 40% w/w, 0 to 36%, 0 to 30% w/w, about 0 to 20% w/w, about 0 to 10% w/w, about 0 to 5% w/w, and about 0 to 2% w/w. Modified fucans also include modified fucans that have a molecular weight distribution such that the portion of about 0 to 5,000 g/mol comprises about 0 to 50% w/w, about 0 to 40% w/w, about 0 to 30% w/w, about 0 to 25% w/w, and about 0 to 20% w/w.

Modified fucans also include modified fucans that have a molecular weight distribution such that the portion of about 0 to 5,000 g/mol comprises less than about 0 to 25% w/w or 0 to 30% w/w. Modified fucans also include modified fucans that have a molecular weight distribution such that the portion of about 5,000 to 60,000 g/mol comprises about 0 to 55% w/w, 5 to 38% w/w, about 10 to 45% w/w, about 15 to 40% w/w, and about 17.5 to 37.5% w/w. Modified fucans also include modified fucans that have a molecular weight distribution such that the portion of about 60,000 to 200,000 g/mol comprises about 0 to 60% w/w, about 0 to 50% w/w, about 0 to 40% w/w, about 5 to 35% w/w, and about 10 to 30% w/w. Modified fucans also include modified fucans that have a molecular weight distribution such that the portion of about 200,000 to 1,600,000 g/mol comprises about 0 to 60% w/w, about 0 to 50% w/w, 8 to 43% w/w, and 10 to 40% w/w. Modified fucans also include modified fucans that have a molecular weight distribution such that the portion of about 1,600,000 g/mol and greater comprises about 0 to 60% w/w, about 0 to 50% w/w, 1 to 33% and about 2.5 to 42.5% w/w. Modified fucans also include modified fucans that have a sulphated content of about 0 to 60% w/w, about 10 to 50% w/w, and about 20 to 40% w/w. Modified fucans also include modified fucans that have a water content of about 0 to 20% w/w, about 0 to 15% w/w, 14 to 40% w/w, or about 0 to 10% w/w. Modified fucans also include modified fucans that have a protein content of about 0 to 12% w/w, 0 to 10% w/w, about 0 to 5% w/w, and about 0 to 2% w/w. Modified fucans also include modified fucans that when made up to a 0.1% w/v solution result in a solution with a pH of about 4 to 8, about 5.5 to 8, about 6 to 8, and about 6 to 7.5.

EXAMPLES

Example 1

Safety and Efficacy of a Selected Fucoidan in Solution Formulation for the Prevention of Surgical Adhesions in Horses Undergoing Celiotomy and Jejenojejunostomy Fucoidan The fucoidan was extracted from the brown marine algae *Undaria pinnatifida* (sourced from Australia).

Methods and Materials for Fucoidan Analysis

Visual examination was used to determine the appearance of the fucoidan. Specific rotation was determined by optical rotation as per USP CSA method <781> using a 3% fucoidan solution. Residue on ignition (sulphated) was determined as per the USP CSA method. Kinematic viscosity was determined using an Ubbelodhe viscometer. Individual sugar monomer content and total carbohydrate content were determined by derivatization and analysis by gas chromatography interfaced with a mass selective detector using electron impact ionization mode. Molecular weight distribution was determined by gel permeation chromatography. Sulphate content of fucoidan was determined by inductively coupled plasma spectroscopy. Loss on drying was determined at approximately 105 degrees Celsius. pH of a 0.1% fucoidan solution was determined as per the USP CSA method.

Methods and Materials for Fucoidan Efficacy and Safety During Horse Abdominal Surgery Twelve horses donated for reasons unrelated to the gastrointestinal tract or abdomen were used. Horses were block randomized and assigned to 1 of 2 experimental groups: (1) fucoidan solution and (2) control LRS (n=6 horses per group). Fucoidan solution and control LRS were prepared by mixing 50 mL of fucoidan concentrate containing 2.5 g of fucoidan or 50 mL of LRS, respectively, into a 5 L bag of LRS and warming to approximately body temperature before surgery.

Horses were treated perioperatively with flunixin meglumine and antimicrobials. A brief abdominal exploration was performed through a 20-cm ventral midline celiotomy incision. At the jejunal segments 10 and 5 arcuate vessels oral to the ileum, a 1-cm full thickness circumferential wedged segment was resected and an anastomosis performed using 2-0 polyglactin 910 in 2-layer simple continuous pattern. The oral anastomosis site was used for mechanical testing and the aboral site for histological evaluation. Prior to closure of the linea alba, 5 L of fucoidan solution or control LRS were infused into the abdomen. The linea alba was apposed using #2 polyglactin 910 in a simple continuous pattern. In the cranial aspect of the linea alba closure, the continuous pattern was interrupted at 8 cm and this segment was used for mechanical testing. The caudal 12 cm was used for histological evaluation. The subcutaneous tissue was apposed using 2-0 polyglactin 910 in a simple continuous pattern.

Postoperatively, feed was gradually reintroduced over 48 hours. A physical examination was performed every 12 hours. Horses were monitored for signs of colic and checked for post-operative reflux (defined as greater than 1 L of reflux at one time) every 8 hours. The incision was subjectively graded for edema, pain on palpation, drainage, and dehiscence. A complete blood count, plasma chemistry, and coagulation profile were performed preoperatively and on days 1, 2, 6, and 10 postoperatively. Horses were euthanized on day 10 postoperatively. Necropsy and pathology results are included in an accompanying abstract.

Horses were euthanized on day 10 postoperatively. Necropsy was performed to evaluate healing and signs of adhesions or infection. The cranial half of the linea alba and the oral anastomosis site were wrapped in sterile saline and refrigerated for immediate mechanical testing. The caudal half of the linea and the aboral anastomosis were fixed in 10% neutral buffered formalin for histological evaluation.

The linea alba was tested in tension, the load to failure recorded (Newtons, N), and then corrected for linea alba length (N/cm). The anastomosis bursting pressure (mmHg) was recorded and bursting wall tension (dynes/cm) calculated. The anastomosis and incision were stained with hematoxylin and eosin and graded for inflammation. Continuous data were analyzed using a one-way analysis of variance. Level of significance was taken as $p<0.05$.

Results for Fucoidan Analysis

Fucoidan was determined to have the following characteristics: appearance was white to off-white powder; specific rotation was negative 68.4 degrees; residue on ignition was approximately 25.9 percent; kinematic viscosity was approximately 2.05 mm^2/s; carbohydrate content was approximately 60.5 percent; fucose content as a percent of total carbohydrate content was approximately 52 percent; galactose content as a percent of total carbohydrate content was approximately 48 percent; remaining sugar monomer content (sum of all sugar monomer content minus fucose and galactose contents) as a percent of total carbohydrate content was approximately less than 1 percent; molecular weight distribution was approximately 8.4 percent between approximately 0 and 5,000 g/mol, approximately 13.4 percent between approximately 5,000 and 60,000 g/mol, approximately 26.5 percent between approximately 60,000 and 200,000 g/mol, approximately 38.7 percent between approximately 200,000 and 1,600,000 g/mol, and approximately 13.2 percent at greater than approximately 1,600,000 g/mol; sulfate content was approximately 30.6 percent; loss on drying was approximately 3.7 percent; pH of 0.1% solution was approximately 6.9.

Results for Fucoidan Efficacy and Safety During Horse Abdominal Surgery

No difference was observed between experimental groups for heart rate or rectal temperature pre-operatively or during the 10 day study period. No difference was observed between experimental groups in the number of colic episodes. There were 2 horses in the fucoidan solution and 3 horses in the LRS control group that had post-operative reflux. The volume of post-operative reflux was greater for the horses in the fucoidan group (23 L in one animal from day 1 to 4; and 139 L in another animal from day 2 to 5) compared to the LRS control group (9.5 L in one animal within the first 24 hours of surgery; 4 L in a second animal one time on day 3 post-operatively; and 5 L in a third animal within the first 72 hours of surgery) and all horses recovered normally. There were no signs at necropsy indicating the cause of the post-operative reflux. The reflux and feces were negative for *Salmonella* spp. One horse in the control group developed an incisional infection and no horses in the fucoidan group had an incisional infection (no statistical difference between treatment groups). There were no signs of peritonitis in any horse. There was no observed difference between experimental groups for fibrinogen concentration, platelet count, activated partial thromboplastin time, gamma glutamyl transferase, aspartate aminotransferase, or creatinine concentration. A difference between groups was determined at several time points for leukocyte and neutrophil count, antithrombin III, prothrombin time, and hematocrit; however, values were generally within normal limits. Although fucoidan is a sulphated polysaccharide (as is heparin), treatment with fucoidan did not negatively impact any of the coagulation parameters.

One horse in the control LRS group had an adhesion between the spleen and the body wall at the site of the incisional infection. There were no other adhesions (no fucoidan group horses had any adhesions). Based on gross necropsy findings there was no difference in anastomosis or incisional healing between groups. Horses in the fucoidan solution group had a significantly higher anastomosis bursting pressure compared to horses in the LRS control group ($262\pm52$ versus $206\pm12$ mmHg, p=0.03) suggesting that fucoidan may have increased healing the anastomosis site. There was also a trend toward horses in the fucoidan solution group having a higher intestinal bursting wall tension compared to horses in the LRS control group ($1,104,000\pm270,000$ versus $941,000\pm189,000$ dynes/cm,); however, this did not reach statistical significance (p=0.29). There was no difference between groups in the tensile load to failure of the linea alba ($67\pm15$ and $64\pm21$ N/cm for fucoidan solution and LRS, respectively, p=0.81). Based on our analysis, there was no difference the amount of inflammation histologically at the anastomosis or linea alba incision.

Fucoidan concentrate and fucoidan solution were simple and easy to use in a clinical setting. Fucoidan reduced the number of animals with adhesions from approximately 17 percent in the control LRS to no animals with adhesion in the fucoidan group. Mechanical testing showed that fucoidan solution did not impair anastomosis or incisional healing and, if anything, the strength of the anastomosis and incision at 10 days was greater than that for the control horses. Fucoidan solution was safely administered intraperitoneally during celiotomy and anastomosis in horses; and we speculate that fucoidan solution may have improved anastomosis healing.

Example 2

Safety and Efficacy of a Fucoidan in Solution Formulation for the Prevention of Surgical Adhesions in Pony Foals Undergoing Intestinal Abrasion Fucoidan The fucoidan was extracted from the brown marine algae *Undaria pinnatifida* (sourced from Australia).

Methods and Materials for Fucoidan Analysis

Visual examination was used to determine the appearance of the fucoidan. Individual sugar monomer content and total carbohydrate content were determined by derivatization and analysis by gas chromatography interfaced with a mass selective detector using electron impact ionization mode. Molecular weight distribution was determined by gel permeation chromatography. Sulphate content of fucoidan was determined by inductively coupled plasma spectroscopy. Acetyal group content was determined by 1H NMR (to provide a quantitative determination of the acetyl groups, the peaks at 1.6 and 2.5 ppm were integrated and the ratio reported as the degree of acetylation).

Methods and Materials for Fucoidan Efficacy and Safety During Pony Foal Abdominal Surgery Surgery was performed on neonate pony foals to induce abdominal adhesions using a serosal abrasion method+catgut suture at four locations on the jejunum. Prior to closing the surgical site 600 mL of a treatment solution were administered intraperitoneally and the surgical site and incision were sutured closed. The treatment groups consisted of control Lactated Ringer's Injection USP (LRS) (n=6) and 0.03% fucoidan dissolved in LRS (n=6). After 10 days a second-look laparoscopy was performed and both the number of adhesions per foal and the characteristics of each adhesion (simple vs. complex) were assessed. A severity score was assigned to adhesion and a total severity score determined for each treatment group. Toxicity of the treatments was investigated by comparing animal weights and haematology parameters (complete blood count including white blood cell differential, coagulation and fibrinogen) between the two treatment groups; and by observing for signs of toxicity (attitude, appetite, rectal temperature, heart rate, etc.).

Results for Fucoidan Analysis

Fucoidan total carbohydrate content was determined to be $51.1\pm5.6$ percent w/w of the fucoidan. Fucoidan individual glycosyl content was determined to be as described in the following table:

| Sugar monomer | Mean amount (percent of total carbohydrate) | Standard deviation (percent of total carbohydrate) |
|---|---|---|
| Fucose | 48.9 | 2.2 |
| Galactose | 47.1 | 2.3 |
| Glucose | 1.4 | 0.4 |
| Mannose | 1.1 | 0.3 |
| Xylose | 0.8 | 0.2 |
| Rhamnose | 0.6 | 0.1 |

Molecular weight distribution of the fucoidan was determined to be as described in the following table:

| Molecular Weight Slice (g/mol) | mean (%) |
|---|---|
| >1,600k | 7.8 |
| 200k-1,600k | 34.7 |
| 60k-200k | 29.8 |
| 5k-60k | 18.9 |
| <5k | 8.7 |

Fucoidan sulfate content was approximately $32.9\pm0.9$ percent w/w. Fucoidan acetyl group content was determined to be such that the ratio of acetyl to fucose was determined to between 0 and 0.3 percent.

Results for Fucoidan Efficacy and Safety During Pony Foal Abdominal Surgery

Fucoidan solution was simple and easy to use in a clinical setting. Foals that had undergone surgery and were treated with 600 mL of 0.03% w/v fucoidan solution had a mean number of adhesions and a total severity score of $2.2\pm1.2$ and $3.5\pm1.5$, respectively, which were both significantly reduced compared with control LRS ($6.2\pm2.5$ and $14.5\pm3.8$, respectively). None of the 13 adhesions observed in the fucoidan solution treated group were complex and 20 of the 37 adhesions observed in the control treated group were complex. No animals were found dead or were euthanized in extremis. No signs of toxicity were observed in any of the animals. There were no differences in haematology parameters between treatment groups save for several small, statistically significant differences within normal limits that were considered to not be clinically relevant. One foal treated with fucoidan solution had segmented neutrophil counts that were above the normal range at 4, 6, 8 and 10 days. Although a segmented neutrophil value at 0 days was not obtained for this animal, the band neutrophil count was higher than normal at this initial timepoint and therefore not deemed to be a result of the treatment. Fucoidan solution was easy to administer and safely prevented the formation of adhesions in the foal abdominal serosal abrasion model of surgical adhesions.

Example 3

Safety and Efficacy of a Fucoidan in Solution Formulation for the Prevention of Surgical Adhesions in Rabbits Undergoing Uterine Horn Surgery Fucoidan Several extracts of fucoidan were prepared from the brown marine algae *Undaria pinnatifida* (sourced from Australia).

Methods and Materials for Fucoidan Analysis

Visual examination was used to determine the appearance of the fucoidan. Molecular weight distribution was determined by gel permeation chromatography. Sulphate content of fucoidan was determined by inductively coupled plasma spectroscopy. Acetyal group content was determined by 1H NMR (to provide a quantitative determination of the acetyl groups, the peaks at 1.6 and 2.5 ppm were integrated and the ratio reported as the degree of acetylation).

Methods and Materials for Fucoidan Efficacy and Safety During Rabbit Abdominal Surgery Rabbits were anesthetized with a mixture of 55 mg/kg ketamine hydrochloride and 5 mg/kb Rompum intramuscularly. Following preparation for sterile surgery, a midline laparotomy was performed. The uterine horse were exteriorized and traumatized by abrasion of the serosal surface with until punctate bleeding developed. Ischemia of both uterine horns was induced by removal of the collateral blood supply. The remaining blood supply to the uterine horns were the ascending branches of the utero-vaginal arterial supply of the myometrium. The horns were then returned to their normal anatomic position and the midline sutured with 3-0 Vicryl. As the incision was closed, a purse string suture was placed around a catheter placed in the incision. Through the catheter, nothing was administered (surgical control) (n=5) or 45 mL of either control Lactated Ringer's Injection USP (control LRS) (n=5) or 0.03% w/v fucoidan in Lactated Ringer's Injection USP (fucoidan solution) (n=5) were placed in the abdomen. Then the final stitch was closed.

After 7 days, the rabbits were terminated and the percentage of the area of the horns adherent to various organs determined. In addition, the tenacity of the adhesions was scored using the following system:

0=No Adhesions

1=mild, easily dissectible adhesions

2=moderate adhesions; non-dissectible, does not tear the organ

3=dense adhesions; non-dissectible, tears organ when removed

In addition an overall score which takes into account all of the above data was given to each rabbit. The following scoring system was used:

| Adhesion Score | Description |
| --- | --- |
| 0 | No adhesions |
| 0.5 | Light, filmy pelvic adhesions involving only one organ, typically only 1 or 2 small adhesions |
| 1.0 | Light, filmy adhesions, not extensive although slightly more extensive than 0.5 |
| 1.5 | Adhesions slightly tougher and more extensive than a 1 rating |
| 2.0 | Tougher adhesions, a little more extensive, uterine horns usually have adhesions to both bowel and bladder |
| 2.5 | Same as 2, except the adhesions are usually not filmy at any site and more extensive |
| 3.0 | Tougher adhesions than 2, more extensive, both horns are attached to the bowel and bladder, some movement of the uterus possible |
| 3.5 | Same as 3, but adhesions slightly more extensive and tougher |
| 4.0 | Severe adhesions, both horns attached to the bowel and bladder, unable to move the uterus without tearing the adhesions |

The rabbits were scored by two independent observers that were blinded to the prior treatment of the animal. If there was disagreement as to the score to be assigned to an individual animal, the higher score was given.

The overall scores were analyzed by rank order analysis and analysis of variance on the ranks. The percentage area of the horns involved to the various organs was compared by Student's t test or one way analysis of variance.

Results for Fucoidan Analysis

The results of the fucoidan appearance, sulphate content, and acetyl group content analysis are included in the following table.

| Treatment | Appearance of Fucoidan Powder used to prepare Treatment | Acetyl (ratio of acetyl to fucose groups, expressed in percent) | Sulphate (percent of material consisting of sulphate) |
| --- | --- | --- | --- |
| Fucoidan extract #AA | Brown powder | 35.9 | 27.1 |
| Fucoidan extract #B | light brown with few crystals | 1.0 | 29.6 |
| Fucoidan extract #C | mixture of light brown powder and flakes | 2.0 | 29.6 |
| Fucoidan extract #D | mixture of dark brown powder and flakes | 1.9 | 29.4 |
| Fucoidan extract #E | light green powder with some larger particles | 1.3 | 30.2 |
| Fucoidan extract #F | light grey-green powder with some larger particles | 0.3 | 29.3 |

-continued

| Treatment | Appearance of Fucoidan Powder used to prepare Treatment | Acetyl (ratio of acetyl to fucose groups, expressed in percent) | Sulphate (percent of material consisting of sulphate) |
|---|---|---|---|
| Fucoidan extract #G | light yellow powder with some larger particles | 0.7 | 29.2 |
| Fucoidan extract #H | light yellow powder with some larger particles | 0.7 | 29.3 |
| Fucoidan extract #I | off white powder | 1.6 | 29.9 |

The results of the fucoidan molecular weight distribution analysis are included in the following table.

| Treatment | <5k (g/mol) | 5k-20k (g/mol) | 20k-60k (g/mol) | 60k-200k (g/mol) | 200k-1,100k (g/mol) | 1,100k-1,600k (g/mol) | >1,600k (g/mol) |
|---|---|---|---|---|---|---|---|
| Fucoidan extract #AA | 14.7 | 5.1 | 13.9 | 23.2 | 24.6 | 3.8 | 14.7 |
| Fucoidan extract #B | 11.1 | 10.7 | 18.7 | 22.7 | 23.5 | 3.1 | 10.2 |
| Fucoidan extract #C | 11.0 | 11.2 | 18.3 | 21.5 | 23.3 | 3.4 | 11.3 |
| Fucoidan extract #D | 12.4 | 12.2 | 18.1 | 19.8 | 21.9 | 3.5 | 12.1 |
| Fucoidan extract #E | 16.7 | 9.0 | 15.3 | 18.6 | 20.3 | 3.2 | 17.1 |
| Fucoidan extract #F | 17.5 | 17.1 | 20.1 | 19.4 | 16.7 | 2.1 | 7.1 |
| Fucoidan extract #G | 16.7 | 16.6 | 17.6 | 18.5 | 18.1 | 2.6 | 9.8 |
| Fucoidan extract #H | 14.3 | 9.0 | 17.1 | 21.5 | 22.8 | 3.3 | 12.1 |
| Fucoidan extract #I | 14.4 | 12.4 | 19.8 | 21.5 | 20.8 | 2.8 | 8.3 |

Results of Fucoidan Efficacy, Safety and Ease of Use During Rabbit Abdominal Surgery Fucoidan solution was simple and easy to use during surgery. The following table summarizes the efficacy of the various fucoidan extracts compared with surgical control and control LRS solution.

| Treatment | Overall adhesion score | Sites free of adhesions (percent) |
|---|---|---|
| Surgical control | 3.1 ± 0.4 | 5.0 |
| Control LRS | 2.8 ± 0.3 | 10.0 |
| Fucoidan extract #AA | 2.2 ± 0.6 | 20.0 |
| Fucoidan extract #B | 1.5 ± 0.4 | 32.5 |
| Fucoidan extract #C | 1.4 ± 0.8 | 40.0 |
| Fucoidan extract #D | 1.6 ± 0.4 | 25.0 |
| Fucoidan extract #E | 1.2 ± 0.3 | 42.5 |
| Fucoidan extract #F | 2.0 ± 0.6 | 17.5 |
| Fucoidan extract #G | 1.3 ± 0.4 | 37.5 |
| Fucoidan extract #H | 1.8 ± 0.4 | 22.5 |
| Fucoidan extract #I | 1.7 ± 0.6 | 15.0 |

No signs of toxicity were observed in any of the fucoidan solution treated animals.

Example 4

Various Fucoidans: Analysis; Safety in Rabbits; Efficacy and Safety in Rabbits Undergoing Surgery; Efficacy and Safety Compared with Sodium Carboxymethylcellulose in Rabbits Undergoing Surgery Fucoidan Extracts of fucoidan were prepared from the brown marine algae *Laminaria japonica* (sourced from China), *Laminaria hyperborean* (sourced from Europe) and *Undaria pinnatifida* (sourced from Korea). As described in detail below, all 3 fucoidans were analyzed; all 3 fucoidans were prepared as solutions and tested for safety in rabbits at 16.7 and 50 mg/kg body weight; all 3 fucoidans were prepared as solutions and tested for efficacy and safety in rabbits at 5 mg/kg body weight; and one fucoidan (*Laminaria hyperborean*) was prepared as a solution (5 mg/kg body weight) and compared with sodium carboxymethylcellulose prepared as a gel for efficacy and safety in rabbits.

Fucoidan Analysis—Methods and Materials

Visual examination was used to determine the appearance of fucoidan. Sulphate content was determined by inductive coupled plasma. Protein content was determined by ultraviolet-visible light (UV-VIS) detection. Fucose, galactose, and other sugar monomer contents, and total carbohydrate content were determined by ultra-high performance liquid chromatography with UV-VIS detection. Molecular weight distributions were determined by gel permeation chromatography with refractive index detection.

Fucoidan Analysis—Results

The results of the fucoidans' appearance, sulphate content, and protein content analysis are included in the following table.

| Species Fucoidan Extracted From | Appearance of Fucoidan Powder | Sulphate (percent of material consisting of sulphate) | Protein content (% w/w) |
|---|---|---|---|
| Laminaria japonica | White to off-white | 14.1 | ~10 |
| Laminaria hyperborean | White to off-white | ~35 | <2 |
| Undaria pinnatifida | Off-white | 35.4 | <2 |

The results of the fucoidans' total carbohydrate, fucose monomer, and galactose monomer content analysis are included in the following table.

| Species Fucoidan Extracted From | Total carbohydrate content (% w/w) | Fucose content (% w/w of total carbohydrate content) | Galactose content (% w/w of total carbohydrate content) |
|---|---|---|---|
| Laminaria japonica | 38.8 | 31.2 | 9.5 |
| Laminaria hyperborean | 37.3 | 68.7 | 28.2 |
| Undaria pinnatifida | 42.2 | 44.1 | 49.3 |

The results of the fucoidans' molecular weight distribution analysis are included in the following table.

| Species Fucoidan Extracted From | <5k g/mol (% w/w) | 5k-60k g/mol (% w/w) | 60k-200k g/mol (% w/w) | 200k-1,600k g/mol (% w/w) | >1,600k g/mol (% w/w) |
|---|---|---|---|---|---|
| Laminaria japonica | 24.9 | 52.6 | 12.9 | 8.2 | 1.4 |
| Laminaria hyperborean | 13.8 | 11.3 | 11.8 | 36.6 | 26.5 |
| Undaria pinnatifida | 11.4 | 5.7 | 12.0 | 42.9 | 28.0 |

Fucoidan Safety in Rabbits—Methods and Materials

The toxicity of the various fucoidans in Lactated Ringer's Injection USP (LRS) was characterized following a single intraperitoneal injection into the New Zealand White rabbit followed by a 14 day observation period.

Group allocation of the rabbits for the study is summarized in the following tabl

| Group Number | Group Designation | Dose Level (mg/kg) | Dose Conc. (mg/mL) | Dose Volume (mL/kg) | Number of animals Male | Number of animals Female |
|---|---|---|---|---|---|---|
| 1 | Control: Lactated Ringer's Injection USP (LRS) | 0 | 0 | 16.7 | 3 | 2 |
| 2 | Fucoidan from Laminaria japonica in LRS - Low Dose | 16.7 | 1 | 16.7 | 2 | 3 |
| 3 | Fucoidan from Laminaria japonica in LRS - High Dose | 50.0 | 3 | 16.7 | 3 | 2 |
| 4 | Fucoidan from Laminaria hyperborean - Low Dose | 16.7 | 1 | 16.7 | 2 | 2 |
| 5 | Fucoidan from Laminaria hyperborean - High Dose | 50.0 | 3 | 16.7 | 0* | 1* |
| 6 | Fucoidan from Undaria pinnatifida - Low Dose | 16.7 | 1 | 16.7 | 2 | 2 |
| 7 | Fucoidan ARC from Undaria pinnatifida - High Dose | 50.0 | 3 | 16.7 | 2 | 2 |

*It may be noted that 2 males and 2 female rabbits were originally allocated to Group 5. However, due to logistical reasons, the 2 males were re-allocated to Groups 1 and 3 and 1 female was re-allocated to Group 2.

During the study, the animals were monitored for possible mortality and clinical signs. Body weight and food consumption were recorded. Blood samples were collected for clinical pathology evaluations (hematology, clinical chemistry and coagulation). Blood samples collected for toxicokinetic evaluation are stored for possible analysis. Necropsies were performed following the observation period and gross observations were recorded.

Fucoidan Safety in Rabbits—Results

There was no mortality in this study. There were no adverse clinical signs noted during the study that were considered to be related to the administration of the 3 different Fucoidan test articles (either at 16.7 or 50 mg/kg) and there was no appreciable difference in body weight gain between treated groups and control. Occasional decreases in appetite were noted in all prior to the start of treatment and so were not related to dose.

There was no test-article related effect on food consumption subsequent to the administration of the 3 different Fucoidan test articles (either at 16.7 or 50.0 mg/kg).

There were no changes in hematological parameters that were considered to be indicative of a Fucoidan test article effect and cell morphology examination did not reveal any findings that were of toxicological significance. There were no changes in coagulation parameters that were considered to be indicative of a test article effect and the changes noted in serum chemistry parameters did not suggest a treatment effect of the 3 different Fucoidan test articles at 16.7 or 50.0 mg/kg.

There were no changes in organ weights that were considered to be indicative of a relationship to treatment.

There were no gross pathology findings in treated animals that were considered to be indicative of an effect of treatment with any of the Fucoidan test articles.

In conclusion, treatment of groups of rabbits at dose levels of 16.7 and 50.0 mg/kg with 3 different Fucoidan test articles extracted from *Laminaria japonica*, *Laminaria hyperborean* and *Undaria pinnatifida*, did not result in mortality or treatment related changes and there were no gross pathology findings in the animals that were considered to be indicative of effect of any of the test articles.

Fucoidan Efficacy and Safety in Rabbits Undergoing Abdominal Surgery—Methods and Materials Surgery was performed on New Zealand White rabbits to induce adhesion formation between the uterine horns and the abdominal sidewall. Prior to closing the surgical site 16.7 mL/kg body weight of a treatment solution were administered intraperitoneally and the surgical site and incision were sutured closed. Treatment groups consisted of 0.03% w/v fucoidan (5 mg fucoidan) extracted from *Laminaria japonica*, *Laminaria hyperborean* and *Undaria pinnatifida* per kg body weight in Lactated Ringer's Injection USP (LRS) and a LRS alone (control) (n=4 per group). After 14 days the animals were euthanized and any adhesions that had formed between the uterine horns and sidewall (termed uterine adhesion score) or elsewhere in the abdomen (termed abdominal adhesion value) were assessed according to standardized scoring methods. Toxicity of the treatments was investigated by comparing animal weights and incision thicknesses between groups; by comparing haematology, blood biochemistry and coagulation parameters' values between groups pre-surgery and at 24 hours and 7 days post-surgery; and by observing for obvious signs of toxicity.

Fucoidan Efficacy and Safety in Rabbits Undergoing Abdominal Surgery—Results

A decrease in uterine adhesion value compared with control LRS was noted in the *Laminaria japonica*, *Laminaria hyperborean* and *Undaria pinnatifida* fucoidan solution groups (18.4±7.8 versus 3.1±1.7, 1.3±1.0, and 2.3±0.5, respectively). A significant decrease in abdominal adhesion values compared with control LRS was noted in the *Laminaria japonica*, *Laminaria hyperborean* and *Undaria pinnatifida* fucoidan solution groups (2.5±1.0 versus 0.9±0.3, 0.8±0.3, and 0.3±0.3, respectively). No animals were found dead or were euthanized in extremis. No difference in animal weights or incision thickness was observed between fucoidan solutions and LRS nor were any obvious signs of toxicity observed in any of the animals. No difference in complete blood counts, blood differentials or coagulation parameters was observed between groups at any time point. A difference in alanine transaminase (ALT) levels between control LRS and *Undaria pinnatifida* (23.0±1.8 versus 16.8±1.0 IU/L, respectively). The difference in ALT levels was likely not clinically relevant. No other difference in any other blood chemistry parameters was observed between groups at any time point. In conclusion, 16.7 mL of 0.03% w/v fucoidan solution (5 mg fucoidan)/kg body weight prepared from *Laminaria japonica*, *Laminaria hyperborean* and *Undaria pinnatifida* was efficacious in preventing the formation of adhesion in the rabbit uterine horn model of surgical adhesions and showed no signs of toxicity.

Fucoidan Compared with Sodium Carboxymethylcellulose for Efficacy and Safety in Rabbits Undergoing Abdominal Surgery—Methods and Materials Sodium carboxylmethylcellulose (SCMC) solution is a viscous gel and during equine abdominal surgeries some veterinary surgeons instill SCMC solution intraperitoneally (IP) immediately before closure of the abdmoninal wall or use part of the SCMC solution to "run the intestine" during the surgery and instill the remainder IP immediately before closure, in an attempt to reduce the formation of post-surgical adhesions. The objective of this study was, using an in vivo model of surgical adhesions, to compare the efficacy and safety of SCMC solution and of fucoidan solution, following administration of the test article IP immediately before closure, or following "running the uterine horns" with a portion of the test article during surgery and administering the remainder of the test article IP immediately before closure, or following administering the two test articles in combination. SCMC type 7H35F PH was obtained from Hercules Inc. Surgery was performed on New Zealand White rabbits to induce adhesion formation between the uterine horns and the abdominal sidewall. Each animal received a total of 16.7 mL test article/kg body weight. (Animals receiving a combination of test articles received a total of 16.7 mL of each test article/kg body weight.) Three different test articles were used in this study: Lactated Ringer's Injection USP (LRS) alone (control solution); 1% w/v SCMC in Water for Injection USP equivalent to 167 mg SCMC/kg body weight (SCMC solution); and, 0.03% w/v fucoidan (from *Laminaria hyperborean*) in LRS equivalent to 5 mg fucoidan/kg body weight (fucoidan solution). Six treatment groups were involved in this study (n=6 per group). Three groups consisted of LRS, fucoidan or SCMC instilled intraperitoneally prior to closure of the abdominal wall. In two groups the solution of fucoidan or SCMC was divided so that 5 ml, of the test article was applied to the uterine horns and the remainder was instilled prior to closure. In one group both SCMC and fucoidan were administered, with 5 mL of the SCMC solution applied to the horns and the remainder, along with the fucoidan, instilled prior to closure. After 14 days the animals were euthanized and any adhesions that had formed between the uterine horns and sidewall (termed uterine adhesion value) or elsewhere in the abdomen (termed abdominal adhesion value) were assessed according to standardized scoring methods. Toxicity of the treatments was investigated by comparing animal weights and incision thicknesses between groups; by comparing haematology, blood biochemistry and coagulation parameters between groups pre-surgery and at 24 hours and 7 days post-surgery; and by observing for obvious clinical signs of toxicity.

Fucoidan Compared with Sodium Carboxymethylcellulose for Efficacy and Safety in Rabbits Undergoing Abdominal Surgery—Results No difference in uterine adhesion score was observed between control LRS and both SCMC solution treatments (20.0±2.8, 19.3±4.1 and 17.3±5.0, respectively). The combination treatment of SCMC solution plus fucoidan solution resulted in a significant decrease in uterine adhesion score (6.1±5.2) compared with control LRS and both SCMC solution treatments. Both fucoidan solution treatments resulted in a significant decrease in uterine adhesion score (2.4±1.1 and 3.0±1.8) compared with all other treatment groups. No difference in abdominal adhesion score was observed between control LRS, both SCMC solution treatments and SCMC solution plus fucoidan solution combination treatment (2.6±2.4, 2.4±1.4, 2.3±1.3 and 2.1±1.1, respectively). Both fucoidan solution treatments resulted in a significant decrease in abdominal adhesion score (0.3±0.5 and 0.2±0.4) compared with all other treatment groups. There was no difference in uterine or abdominal adhesion scores between the two fucoidan solution treatments. No difference in animal weights or incision thickness was observed between any of the treatment groups and the control LRS group nor were any obvious signs of toxicity observed in any of the animals. No difference in complete blood counts, differentials or blood chemistry parameters was observed between control LRS and treated groups at any time point.

An increase in activated partial thromboplastin time (APTT) was observed between pre-surgery and 24 hour values within the control LRS group, both SCMC solution treatments, and the SCMC solution plus fucoidan solution combination treatment, but not within the two fucoidan groups. In conclusion, SCMC solution treatments had no effect on adhesions; SCMC solution plus fucoidan (from *Laminaria hyperborean*) solution combination treatment resulted in an approximately 70% decrease in uterine adhesion values but had no effect on abdominal adhesion values; and fucoidan (from *Laminaria hyperborean*) solution treatments resulted in an approximately 90% decrease in adhesion formation, in the rabbit uterine horn sidewall surgical adhesion model. No difference in efficacy was observed between instilling fucoidan solution IP immediately prior to closure or using part of the fucoidan solution to "run the uterine horns" and administering the remainder IP immediately prior to closure. Fucoidan solution, alone or in combination with SCMC, showed no signs of toxicity.

Example 5

Efficacy of a Selected Fucoidan Solution Formulation for Horse with Peritonitis

The fucoidan is extracted from the brown marine algae *Undaria pinnatifida* and using the analysis techniques described in previous examples the fucoidan is determined to have the characteristics given in the following table:

| Test | Result |
|---|---|
| Appearance | White to off-white powder |
| Total carbohydrate content | 61 percent w/w |
| Fucose content | 52 percent w/w of total carbohydrate |
| Galactose content | 48 percent w/w of total carbohydrate |
| Other sugar monomers | Less than 1 percent w/w of total carbohydrate |
| Molecular weight of carbohydrates | |
| <5k g/mol | 8 percent w/w |
| 5k-20k g/mol | 2 percent w/w |
| 20k-60k g/mol | 11 percent w/w |
| 60k-200k g/mol | 27 percent w/w |
| 200k-1,100k g/mol | 35 percent w/w |
| 1,000k-1,600 g/mol | 4 percent w/w |
| >1,600k g/mol | 13 percent w/w |
| Sulphate content | 31 percent w/w |
| Ratio of acetyl:fucose (percent) | Less than 2 percent |
| Water content | Less than 10 percent w/w |
| pH of a 0.1% w/v solution | 7 |

Fucoidan solution is prepared by dissolving 5 g fucoidan in 50 mL Lactated Ringer's Injection USP, sterilizing by autoclave, and allowing the solution to cool to ambient temperature. A horse with peritonitis including the symptoms of peritonitis such as abdominal pain, abdominal tenderness and abdominal guarding is injected intravenously with fucoidan solution via intravenous drip over 30 minutes. Following treatment with fucoidan solution the peritonitis and symptoms of peritonitis in the horse decrease.

Example 6

Efficacy of a Fucoidan Solution Formulation for a Horse with Peritonitis

The fucoidan is extracted from the brown marine algae *Undaria pinnatifida* and using the analysis techniques described in previous examples the fucoidan is determined to have the characteristics given in the following table:

| Test | Result |
|---|---|
| Appearance | White to off-white powder |
| Total carbohydrate content | 61 percent w/w |
| Fucose content | 52 percent w/w of total carbohydrate |
| Galactose content | 48 percent w/w of total carbohydrate |
| Other sugar monomers | Less than 1 percent w/w of total carbohydrate |
| Molecular weight of carbohydrates | |
| <5k g/mol | 8 percent w/w |
| 5k-20k g/mol | 2 percent w/w |
| 20k-60k g/mol | 11 percent w/w |
| 60k-200k g/mol | 27 percent w/w |
| 200k-1,100k g/mol | 35 percent w/w |
| 1,000k-1,600 g/mol | 4 percent w/w |
| >1,600k g/mol | 13 percent w/w |
| Sulphate content | 31 percent w/w |
| Ratio of acetyl:fucose (percent) | Less than 2 percent |
| Water content | Less than 10 percent w/w |
| pH of a 0.1% w/v solution | 7 |

Fucoidan solution is prepared by dissolving 5 g fucoidan in 50 mL Lactated Ringer's Injection USP, sterilizing by autoclave, and allowing the solution to cool to ambient temperature. A horse with peritonitis including the symptoms of peritonitis such as abdominal pain, abdominal tenderness and abdominal guarding is administered 50 mL of fucoidan solution via intra-abdominal injection. Following treatment with fucoidan solution the peritonitis and symptoms of peritonitis in the horse decrease.

Example 7

Efficacy of a Fucoidan Solution Formulation for Horse with Ischemia

The fucoidan is extracted from the brown marine algae *Undaria pinnatifida* and using the analysis techniques described in previous examples the fucoidan is determined to have the characteristics given in the following table:

| Test | Result |
|---|---|
| Appearance | White to off-white powder |
| Total carbohydrate content | 61 percent w/w |
| Fucose content | 52 percent w/w of total carbohydrate |
| Galactose content | 48 percent w/w of total carbohydrate |
| Other sugar monomers | Less than 1 percent w/w of total carbohydrate |
| Molecular weight of carbohydrates | |
| <5k g/mol | 8 percent w/w |
| 5k-20k g/mol | 2 percent w/w |
| 20k-60k g/mol | 11 percent w/w |
| 60k-200k g/mol | 27 percent w/w |
| 200k-1,100k g/mol | 35 percent w/w |
| 1,000k-1,600 g/mol | 4 percent w/w |
| >1,600k g/mol | 13 percent w/w |
| Sulphate content | 31 percent w/w |
| Ratio of acetyl:fucose (percent) | Less than 2 percent |
| Water content | Less than 10 percent w/w |
| pH of a 0.1% w/v solution | 7 |

Fucoidan solution is prepared by dissolving 5 g fucoidan in 50 mL Lactated Ringer's Injection USP, sterilizing by autoclave, and allowing the solution to cool to ambient temperature. A horse with ischemia including injected intravenously with 50 mL fucoidan solution via intravenous drip over 30 minutes. Following treatment with fucoidan solution the ischemia in the horse decreases.

Example 8

Efficacy of a Fucoidan Solution Formulation for Horse with Reperfusion Injury

The fucoidan is extracted from the brown marine algae *Undaria pinnatifida* and using the analysis techniques described in previous examples the fucoidan is determined to have the characteristics given in the following table:

| Test | Result |
|---|---|
| Appearance | White to off-white powder |
| Total carbohydrate content | 61 percent w/w |
| Fucose content | 52 percent w/w of total carbohydrate |
| Galactose content | 48 percent w/w of total carbohydrate |
| Other sugar monomers | Less than 1 percent w/w of total carbohydrate |
| Molecular weight of carbohydrates | |
| <5k g/mol | 8 percent w/w |
| 5k-20k g/mol | 2 percent w/w |
| 20k-60k g/mol | 11 percent w/w |
| 60k-200k g/mol | 27 percent w/w |
| 200k-1,100k g/mol | 35 percent w/w |
| 1,000k-1,600 g/mol | 4 percent w/w |
| >1,600k g/mol | 13 percent w/w |
| Sulphate content | 31 percent w/w |
| Ratio of acetyl:fucose (percent) | Less than 2 percent |
| Water content | Less than 10 percent w/w |
| pH of a 0.1% w/v solution | 7 |

Fucoidan solution is prepared by dissolving 5 g fucoidan in 50 mL Lactated Ringer's Injection USP, sterilizing by autoclave, and allowing the solution to cool to ambient temperature. Horses with ischemia that are to undergo reperfusion treatment are each injected intravenously with 50 mL of either fucoidan solution or control Lactated Ringer's Injection USP via intravenous drip over 30 minutes, immediately before reperfusion treatment. The horses that receive fucoidan solution have a decrease in reperfusion injury compared with the horses receiving control Lactated Ringer's Injection USP.

Example 9

Efficacy of a Fucoidan Solution Formulation for Horse with Endotoxemia

The fucoidan is extracted from the brown marine algae *Undaria pinnatifida* and using the analysis techniques described in previous examples the fucoidan is determined to have the characteristics given in the following table:

| Test | Result |
|---|---|
| Appearance | White to off-white powder |
| Total carbohydrate content | 61 percent w/w |
| Fucose content | 52 percent w/w of total carbohydrate |
| Galactose content | 48 percent w/w of total carbohydrate |
| Other sugar monomers | Less than 1 percent w/w of total carbohydrate |
| Molecular weight of carbohydrates | |
| <5k g/mol | 8 percent w/w |
| 5k-20k g/mol | 2 percent w/w |
| 20k-60k g/mol | 11 percent w/w |
| 60k-200k g/mol | 27 percent w/w |
| 200k-1,100k g/mol | 35 percent w/w |
| 1,000k-1,600 g/mol | 4 percent w/w |
| >1,600k g/mol | 13 percent w/w |
| Sulphate content | 31 percent w/w |
| Ratio of acetyl:fucose (percent) | Less than 2 percent |
| Water content | Less than 10 percent w/w |
| pH of a 0.1% w/v solution | 7 |

Fucoidan solution is prepared by dissolving 5 g fucoidan in 50 mL Lactated Ringer's Injection USP, sterilizing by autoclave, and allowing the solution to cool to ambient temperature. A horse with endotoxemia including the symptoms of endotoxemia such as septic shock is injected intravenously with 50 mL of fucoidan solution via intravenous drip over 30 minutes. Following treatment with fucoidan solution the endotoxemia and symptoms of endotoxemia in the horse decrease.

Example 10

Efficacy of a Fucoidan Solution Formulation for a Person with Keloid Trait

The fucoidan is extracted from the brown marine algae *Undaria pinnatifida* and using the analysis techniques described in previous examples the fucoidan is determined to have the characteristics given in the following table:

| Test | Result |
|---|---|
| Appearance | White to off-white powder |
| Total carbohydrate content | 61 percent w/w |
| Fucose content | 52 percent w/w of total carbohydrate |
| Galactose content | 48 percent w/w of total carbohydrate |
| Other sugar monomers | Less than 1 percent w/w of total carbohydrate |
| Molecular weight of carbohydrates | |
| <5k g/mol | 8 percent w/w |
| 5k-20k g/mol | 2 percent w/w |
| 20k-60k g/mol | 11 percent w/w |
| 60k-200k g/mol | 27 percent w/w |
| 200k-1,100k g/mol | 35 percent w/w |
| 1,000k-1,600 g/mol | 4 percent w/w |
| >1,600k g/mol | 13 percent w/w |
| Sulphate content | 31 percent w/w |
| Ratio of acetyl:fucose (percent) | Less than 2 percent |
| Water content | Less than 10 percent w/w |
| pH of a 0.1% w/v solution | 7 |

Fucoidan solution is prepared by dissolving 5 g fucoidan in 50 mL Lactated Ringer's Injection USP, sterilizing by autoclave, and allowing the solution to cool to ambient temperature. A person with keloid trait including the symptoms of keloid trait such as raised scars is injected subcutaneously, locally at the site of the raised scars with 0.5 mL of fucoidan solution per subcutaneous injection. Following treatment with fucoidan solution the raised scars decrease in severity.

Example 11

Efficacy of a Fucoidan Solution Formulation for a Person with Keloid (Keloid Scar)

The fucoidan is extracted from the brown marine algae *Undaria pinnatifida* and using the analysis techniques described in previous examples the fucoidan is determined to have the characteristics given in the following table:

| Test | Result |
|---|---|
| Appearance | White to off-white powder |
| Total carbohydrate content | 61 percent w/w |
| Fucose content | 52 percent w/w of total carbohydrate |
| Galactose content | 48 percent w/w of total carbohydrate |
| Other sugar monomers | Less than 1 percent w/w of total carbohydrate |
| Molecular weight of carbohydrates | |
| <5k g/mol | 8 percent w/w |
| 5k-20k g/mol | 2 percent w/w |
| 20k-60k g/mol | 11 percent w/w |
| 60k-200k g/mol | 27 percent w/w |
| 200k-1,100k g/mol | 35 percent w/w |
| 1,000k-1,600 g/mol | 4 percent w/w |
| >1,600k g/mol | 13 percent w/w |
| Sulphate content | 31 percent w/w |
| Ratio of acetyl:fucose (percent) | Less than 2 percent |
| Water content | Less than 10 percent w/w |
| pH of a 0.1% w/v solution | 7 |

Fucoidan solution is prepared by dissolving 5 g fucoidan in 50 mL Lactated Ringer's Injection USP, sterilizing by autoclave, and allowing the solution to cool to ambient temperature. A person with keloids (keloid scars) is injected subcutaneously, locally at the site of the keloid scars with 0.5 mL of fucoidan solution per subcutaneous injection. Following treatment with fucoidan solution the keloid scars decrease in severity.

Example 12

Efficacy of a Fucoidan Solution Formulation for a Person with Seborrhoeic Dermatitis (Dandruff)

The fucoidan is extracted from the brown marine algae *Undaria pinnatifida* and using the analysis techniques described in previous examples the fucoidan is determined to have the characteristics given in the following table:

| Test | Result |
|---|---|
| Appearance | White to off-white powder |
| Total carbohydrate content | 61 percent w/w |
| Fucose content | 52 percent w/w of total carbohydrate |
| Galactose content | 48 percent w/w of total carbohydrate |
| Other sugar monomers | Less than 1 percent w/w of total carbohydrate |
| Molecular weight of carbohydrates | |
| <5k g/mol | 8 percent w/w |
| 5k-20k g/mol | 2 percent w/w |
| 20k-60k g/mol | 11 percent w/w |
| 60k-200k g/mol | 27 percent w/w |
| 200k-1,100k g/mol | 35 percent w/w |
| 1,000k-1,600 g/mol | 4 percent w/w |
| >1,600k g/mol | 13 percent w/w |
| Sulphate content | 31 percent w/w |
| Ratio of acetyl:fucose (percent) | Less than 2 percent |
| Water content | Less than 10 percent w/w |
| pH of a 0.1% w/v solution | 7 |

Fucoidan solution is prepared by dissolving 5 g fucoidan in 50 mL Lactated Ringer's Injection USP, sterilizing by autoclave, and allowing the solution to cool to ambient temperature. A person with seborrhoeic dermatitis (dandruff) applies 5 mL of fucoidan solution topically at the site of seborrhoeic dermatitis, daily for 5 days. Following treatment with fucoidan solution the seborrhoeic dermatitis decreases.

Example 13

Efficacy of a Fucoidan Solution Formulation for a Person with Contact Dermatitis The fucoidan is extracted from the brown marine algae *Undaria pinnatifida* and using the analysis techniques described in previous examples the fucoidan is determined to have the characteristics given in the following table:

| Test | Result |
|---|---|
| Appearance | White to off-white powder |
| Total carbohydrate content | 61 percent w/w |
| Fucose content | 52 percent w/w of total carbohydrate |
| Galactose content | 48 percent w/w of total carbohydrate |
| Other sugar monomers | Less than 1 percent w/w of total carbohydrate |
| Molecular weight of carbohydrates | |
| <5k g/mol | 8 percent w/w |
| 5k-20k g/mol | 2 percent w/w |
| 20k-60k g/mol | 11 percent w/w |
| 60k-200k g/mol | 27 percent w/w |
| 200k-1,100k g/mol | 35 percent w/w |

-continued

| Test | Result |
| --- | --- |
| 1,000k-1,600 g/mol | 4 percent w/w |
| >1,600k g/mol | 13 percent w/w |
| Sulphate content | 31 percent w/w |
| Ratio of acetyl:fucose (percent) | Less than 2 percent |
| Water content | Less than 10 percent w/w |
| pH of a 0.1% w/v solution | 7 |

Fucoidan cream is prepared by thoroughly mixing 5 g fucoidan in 50 mL of Dermabase Cream. A person with contact dermatitis and symptoms of red, itchy skin applies 5 mL of fucoidan cream topically at the site of contact dermatitis, daily for 5 days. Following treatment with fucoidan cream the contact dermatitis including its symptoms decreases.

Example 30

Efficacy of a Fucoidan Solution Formulation for a Person with Rosacea

The fucoidan is extracted from the brown marine algae *Undaria pinnatifida* and using the analysis techniques described in previous examples the fucoidan is determined to have the characteristics given in the following table:

| Test | Result |
| --- | --- |
| Appearance | White to off-white powder |
| Total carbohydrate content | 61 percent w/w |
| Fucose content | 52 percent w/w of total carbohydrate |
| Galactose content | 48 percent w/w of total carbohydrate |
| Other sugar monomers | Less than 1 percent w/w of total carbohydrate |
| Molecular weight of carbohydrates | |
| <5k g/mol | 8 percent w/w |
| 5k-20k g/mol | 2 percent w/w |
| 20k-60k g/mol | 11 percent w/w |
| 60k-200k g/mol | 27 percent w/w |
| 200k-1,100k g/mol | 35 percent w/w |
| 1,000k-1,600 g/mol | 4 percent w/w |
| >1,600k g/mol | 13 percent w/w |
| Sulphate content | 31 percent w/w |
| Ratio of acetyl:fucose (percent) | Less than 2 percent |
| Water content | Less than 10 percent w/w |
| pH of a 0.1% w/v solution | 7 |

Fucoidan cream is prepared by thoroughly mixing 5 g fucoidan in 50 mL of Dermabase Cream. A person with early stage rosacea and symptoms of red, itchy skin on their bald head applies 5 mL of fucoidan cream topically at the site of rosacea, daily for 5 days. Following treatment with fucoidan cream the rosacea including its symptoms decreases.

Unless expressly stated otherwise or clear from the context, all embodiments, aspects, features, etc., can be mixed and matched, combined and permuted in any desired manner. Unless indicated otherwise, except within the claims, the use of "or" includes "and" and vice-versa. Non-limiting terms are not to be construed as limiting unless expressly stated, or the context clearly indicates, otherwise. (For example, "including," "having," and "comprising" typically indicate "including without limitation".) Singular forms, including in the claims, such as "a," "an," and "the" include the plural reference unless expressly stated, or the context clearly indicates, otherwise.

What is claimed is:

1. A medical composition comprising a therapeutically effective amount of a fucan in combination with at least one pharmaceutically acceptable excipient, filler, carrier or diluent, wherein the fucan has a sulphate content between 14 to 40% w/w and a total carbohydrate content between 37 to 75% w/w, wherein the carbohydrate comprises each of fucose, galactose, glucose, mannose, xylose and rhamnose; and wherein the fucan comprises a molecular weight distribution wherein the portion from 0 to 5,000 g/mol comprises between 0 to 25% w/w, the portion from 5,000 to 60,000 g/mol comprises between 5 to 38% w/w, the portion from 60,000 to 200,000 g/mol comprises between 10 to 30% w/w, the portion from 200,000 to 1,600,000 g/mol comprises between 8 to 43% w/w, and the portion from more than 1,600,000 g/mol comprises between 1 to 33% w/w.

2. The medical composition of claim 1 wherein the fucan has a fucose content as a percentage of total carbohydrate content between 31 to 71% w/w.

3. The medical composition of any one of claims 1 to 2 wherein the fucan has a galactose content as a percentage of total carbohydrate content between 9 to 46% w/w.

4. The medical composition of any one of claims 1 to 2 wherein the fucan has a sugar content excluding fucose and galactose as a percentage of total carbohydrate content between 0 to 59% w/w.

5. The medical composition of any one of claims 1 to 2 wherein the fucan has an acetyl content as a ratio of acetyl:fucose between 0 to 36%.

6. The medical composition of any one of claims 1 to 2 wherein the fucan when prepared as a 0.1% w/v solution has a pH of 4 to 8.

7. The medical composition of any one of claims 1 to 2 wherein the fucan has a protein content between 0 to 12% w/w.

8. The medical composition of any one of claims 1 to 2 wherein the fucan has an appearance of white, off-white, light yellow, light orange, or light green.

9. The medical composition of any one of claims 1 to 2 wherein the composition is a solution, gel, sol or suspension with a fucan concentration between 0.001 to 10% w/v.

10. The composition of claim 9 wherein the fucan concentration is 5% w/v.

11. The composition of claim 9 wherein the fucan concentration is between 0.001 and 1% w/v.

12. The composition of claim 11 wherein the fucan concentration is 0.05% w/v.

13. The composition of claim 11 wherein the fucan concentration is 0.03% w/v.

14. A kit comprising a therapeutically effective amount of the composition of any one of claims 1 to 2 in a vessel configured to administer at least one dose of the composition to an animal, the kit further comprising at least one label comprising instructions for the administration.

15. The kit of claim 14, wherein the instructions direct treatment of at least one of fibrous adhesions, peritonitis, ischemia, reperfusion injury, endotoxemia, keloid trait scarring, keloids, dermatitis, and rosacea.

16. An isolated and purified composition according to any one of claims 1 to 2 for use in the manufacture of a medicament for inhibiting or treating a proliferative or inflammatory disease in a human patient.

17. The composition of claim 16 wherein the disease is at least one of fibrous adhesions, peritonitis, ischemia, reperfusion injury, endotoxemia, keloid trait scarring, keloids, dermatitis, and rosacea.

18. The composition of claim 16 wherein the composition is a solution, gel, sol, suspension, spray, mousse, lotion, cream, ointment, paste, slurry, particulate, microparticulate, microsphere, film, slab, wrap, barrier or implant.

19. The medical composition of claim 1 wherein the fucan is prepared from the brown marine algae *Laminaria hyperborean*.

20. The medical composition of claim 1 wherein the fucan is prepared from the brown marine algae *Laminaria japonica*.

21. The medical composition of claim 1 wherein the fucan is prepared from the brown marine algae *Undaria pinnatifida*.

22. A medical composition comprising a therapeutically effective amount of a fucan in combination with at least one pharmaceutically acceptable excipient, filler, carrier or diluent, wherein the fucan has a sulphate content between 0.001 to 60% w/w and a total carbohydrate content between 37 to 75% w/w; a fucose content as a percentage of total carbohydrate content between 31 to 71% w/w; an acetyl group content of 0.001 to 2% w/w; a protein content of 0.001 to 2% w/w; and an appearance of white to off-white or white to light brown; and when made up to a 0.1% w/v solution result in a solution with a pH of 4 to 8, wherein the carbohydrate comprises each of fucose, galactose, glucose, mannose, xylose and rhamnose.

23. The medical composition of claim 22 wherein the fucan has a molecular weight distribution wherein the portion from 0 to 5,000 g/mol comprises between 0.001 to 25% w/w, the portion from 5,000 to 60,000 g/ml comprises between 0.001 to 55% w/w, the portion from 60,000 to 200,000 g/mol comprises between 0.001 to 40% w/w, the portion from 200,000 to 1,600,000 g/mol comprises between 0.001 to 60% w/w and the portion from more than 1,600,000 g/mol comprises between 0.1 to 50% w/w.

24. The medical composition of claim 22 wherein the fucan is prepared from the brown marine algae *Laminaria hyperborean*.

25. The medical composition of claim 22 wherein the fucan is prepared from the brown marine algae *Laminaria japonica*.

26. The medical composition of claim 22 wherein the fucan is prepared from the brown marine algae *Undaria pinnatifida*.

27. A medical composition comprising a therapeutically effective amount of a fucan in combination with at least one pharmaceutically acceptable excipient, filler, carrier or diluent, wherein the fucan has a sulphate content between 0.001 to 60% w/w and a total carbohydrate content between 37 to 75% w/w; a fucose content as a percentage of total carbohydrate content between 31 to 71% w/w; an acetyl group content of 0% w/w; and a protein content of 0% w/w; an appearance of white to off-white or white to light brown; and when made up to a 0.1% w/v solution result in a solution with a pH of 4 to 8, wherein the carbohydrate comprises each of fucose, galactose, glucose, mannose, xylose and rhamnose.

28. The medical composition of claim 27 wherein the fucan has a molecular weight distribution wherein the portion from 0 to 5,000 g/mol comprises between 0.001 to 25% w/w, the portion from 5,000 to 60,000 g/ml comprises between 0.001 to 55% w/w, the portion from 60,000 to 200,000 g/mol comprises between 0.001 to 40% w/w, the portion from 200,000 to 1,600,000 g/mol comprises between 0.001 to 60% w/w and the portion from more than 1,600,000 g/mol comprises between 0.001 to 50% w/w.

29. The medical composition of claim 27 wherein the fucan is prepared from the brown marine algae *Laminaria hyperborean*.

30. The medical composition of claim 27 wherein the fucan is prepared from the brown marine algae *Laminaria japonica*.

31. The medical composition of claim 27 wherein the fucan is prepared from the brown marine algae *Undaria pinnatifida*.

* * * * *